(12) United States Patent
Lin et al.

(10) Patent No.: US 7,615,663 B2
(45) Date of Patent: *Nov. 10, 2009

(54) OPTIMIZED PRODUCTION OF AROMATIC DICARBOXYLIC ACIDS

(75) Inventors: Robert Lin, Kingsport, TN (US); Ruairi Seosamh O'Meadhra, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 313 days.

This patent is subject to a terminal disclaimer.

(21) Appl. No.: 11/191,766

(22) Filed: Jul. 28, 2005

(65) Prior Publication Data

US 2006/0047166 A1  Mar. 2, 2006

Related U.S. Application Data

(60) Provisional application No. 60/606,735, filed on Sep. 2, 2004, provisional application No. 60/606,807, filed on Sep. 2, 2004.

(51) Int. Cl.
  *C07C 51/42* (2006.01)
(52) U.S. Cl. ............................................. 562/485
(58) Field of Classification Search .................. None
  See application file for complete search history.

(56) References Cited

U.S. PATENT DOCUMENTS

| | | | |
|---|---|---|---|
| 2,794,832 A | 6/1957 | Kornalis | |
| 2,962,361 A | 11/1960 | Spiller et al. | |
| 3,629,321 A * | 12/1971 | Longland et al. | 560/77 |
| 3,859,344 A | 1/1975 | Shigeyasu et al. | |
| 3,873,275 A | 3/1975 | Bennett | |
| 4,241,220 A | 12/1980 | Itaya et al. | |
| 4,334,086 A | 6/1982 | Hanotier et al. | |
| 4,835,307 A * | 5/1989 | Lindahl et al. | 562/413 |
| 5,132,450 A | 7/1992 | Tanaka et al. | |
| 5,359,133 A * | 10/1994 | Nazimok et al. | 562/413 |
| 5,712,412 A | 1/1998 | Inary et al. | |
| 5,777,161 A | 7/1998 | Inary | |
| RE36,008 E | 12/1998 | Hindmarsh et al. | |
| 6,054,610 A | 4/2000 | Lee et al. | |
| 6,307,099 B1 | 10/2001 | Turner et al. | |
| 6,562,997 B2 | 5/2003 | Sikkenga et al. | |
| 2001/0041811 A1 | 11/2001 | Sikkenga et al. | |
| 2003/0004372 A1 | 1/2003 | Piras et al. | |
| 2003/0180202 A1 | 9/2003 | Ellen et al. | |

FOREIGN PATENT DOCUMENTS

| | | |
|---|---|---|
| EP | 321272 A1 | 12/1988 |
| JP | 59093029 | 5/1984 |

(Continued)

OTHER PUBLICATIONS

Perry, R.H.; Green, D.W. (1997) Perry's Chemical Engineers' Handbook (7th Edition). McGraw-Hill. 19 (1-65).*

*Primary Examiner*—Karl J Puttlitz
(74) *Attorney, Agent, or Firm*—Jennifer R. Knight; Bernard J. Graves, Jr.

(57) ABSTRACT

Disclosed is an optimized process and apparatus for more efficiently producing and purifying aromatic dicarboxylic acids (e.g., terephthalic acid). The optimized system employs at least one zoned slurry concentrator to enhance purification of the aromatic dicarboxylic acid.

35 Claims, 6 Drawing Sheets

FOREIGN PATENT DOCUMENTS

| | | |
|---|---|---|
| WO | WO 93/19826 | 10/1993 |
| WO | WO 98/38150 | 9/1998 |
| WO | WO 2004/052820 A1 | 6/2004 |
| WO | WO 2004/058377 A1 | 7/2004 |
| WO | WO 2004/103945 A1 | 12/2004 |

* cited by examiner

OPTIMIZED PRODUCTION OF AROMATIC DICARBOXYLIC ACIDS

RELATED APPLICATIONS

This application claims the priority benefit of U.S. Provisional patent application Ser. Nos. 60/606,735 and 60/606,807, both filed Sep. 2, 2004, the entire disclosures of which are incorporated herein by reference.

FIELD OF THE INVENTION

This invention relates generally to the production of aromatic dicarboxylic acids, such as terephthalic acid (TPA). One aspect of the invention concerns a process and apparatus for more efficiently and/or effectively purifying crude aromatic dicarboxylic acids, such as crude terephthalic acid (CTA). Another aspect of the invention concerns a more economical system for producing purified aromatic dicarboxylic acids, such as purified terephthalic acid (PTA).

BACKGROUND OF THE INVENTION

Terephthalic acid (TPA) is one of the basic building blocks in the production of linear polyester resins used in the manufacture of polyester films, packaging materials, and bottles. TPA used in the manufacture of such polyesters resins must meet certain minimum purity requirements.

The purified condition of TPA refers primarily to the absence of significant concentrations of 4-carboxybenzaldehyde (4-CBA) and para-toluic acid (p-TAc) that are present in significant quantities in the commercially-available crude grades of TPA. Both 4-CBA and p-TAc are partial oxidation products formed in the manufacture of TPA by the catalytic oxidation of para-xylene. The purified form of TPA also refers to the absence of color bodies that impart a characteristic yellow hue to the crude material. The color bodies are aromatic compounds having the structures of benzils, fluorenones, and/or anthraquinones. 4-CBA and p-TAc are particularly detrimental to the polymerization process because they act as chain terminators during the condensation reaction between TPA and ethylene glycol in the production of polyethylene terephthalate (PET).

In a typical process for producing TPA, a crude slurry is withdrawn from the primary oxidation reactor. The crude slurry contains a liquid mother liquor and solid particles of crude terephthalic acid (CTA). The liquid mother liquor exiting the primary oxidation reactor typically contains a significant amount of impurities. Thus, in many conventional TPA production processes, a substantial portion of the liquid mother liquor exiting the primary oxidation reactor is replaced/displaced with a "clean" replacement solvent prior to purification of the CTA particles. This replacement/displacement of the liquid mother liquor in the crude slurry with a replacement solvent is commonly known as "liquor exchange."

Conventional devices employed to perform liquor exchange can be both expensive and unreliable. One common device used to perform liquor exchange is a disc stack centrifuge system. Although effective for replacing the original mother liquor with a replacement solvent, the high-velocity rotating components of such mechanical centrifuge systems cause them to be expensive and unreliable. Thus, a CTA purification system that eliminates the use of one or more mechanical centrifuges would have a lower capital cost and higher reliability than conventional CTA purification systems. Further, if the liquor exchange function typically provided by a mechanical centrifuge could be combined with other functions of a CTA purification system, the overall cost of the system could be reduced while increasing its reliability. Finally, if one or more mechanical centrifuges could be replaced by mechanisms that more effectively replace impurity-laden mother liquor with clean replacement solvent, a purer TPA product could be produced.

SUMMARY OF THE INVENTION

One embodiment of the present invention concerns a process comprising the following steps: (a) oxidizing one or more reactants in a primary oxidation reactor to thereby produce a solid/liquid mixture comprising CTA particles; and (b) subjecting at least a portion of the solid/liquid mixture to oxidative digestion in a zoned slurry concentrator, thereby producing a solids-concentrated mixture containing oxidation-treated TPA particles.

Another embodiment of the present invention concerns a process comprising the following steps: (a) introducing a feed slurry into a zoned slurry concentrator, wherein the feed slurry comprises solid TPA particles; (b) withdrawing a liquid-concentrated mixture from a liquids outlet of the zoned slurry concentrator; and (c) withdrawing a solids-concentrated mixture from a solids outlet of the zoned slurry concentrator, wherein the ratio of the solids content of the solids-concentrated mixture to the solids content of the liquid-concentrated mixture is at least about 2:1 by weight.

Still another embodiment of the present invention concerns a process comprising the following steps: (a) oxidizing para-xylene in a primary oxidation reactor to thereby produce an initial solid/liquid mixture containing CTA particles; (b) subjecting at least a portion of the initial solid/liquid mixture to oxidative digestion in an initial digester to thereby produce an initial digested solid/liquid mixture; (c) subjecting at least a portion of the initial digested solid/liquid mixture to oxidative digestion in a zoned slurry concentrator; (d) withdrawing a liquid-concentrated mixture from a liquids outlet of the zoned slurry concentrator, wherein the ratio of the solids content of the initial digested solid/liquid mixture to the solids content of the liquid-concentrated mixture is at least about 1.5:1 by weight; (e) withdrawing a solids-concentrated mixture from a solids outlet of the zoned slurry concentrator; and (f) introducing a dilution liquid into the solids-concentrated mixture to thereby produce a diluted mixture having a solids content less than the solids content of the solids-concentrated mixture.

Yet another embodiment of the present invention concerns an apparatus for producing and purifying a solid/liquid mixture containing CTA particles. The system includes a primary oxidation reactor for producing the solid/liquid mixture and a zoned slurry concentrator. The zoned slurry concentrator comprises a vessel shell, an upright baffle, a feed inlet, a liquids outlet, and a solids outlet. The vessel shell defines an internal volume. The upright baffle is disposed in the vessel shell and separates at least a portion of the internal volume into a settling zone and an agitated zone. The feed inlet receives at least a portion of the solid/liquid mixture from the primary oxidation reactor and discharges the portion into the agitated zone. The liquids outlet is positioned proximate the settling zone. The solids outlet is positioned below the liquids outlet.

DETAILED DESCRIPTION

FIGS. 1 and 4-6 illustrate embodiments of the present invention where terephthalic acid (TPA) produced in a primary/initial oxidation reactor is purified in a system employing at least one zoned slurry concentrator. Zoned slurry concentrators are described in detail below with reference to FIGS. 2 and 3.

Figure 1:
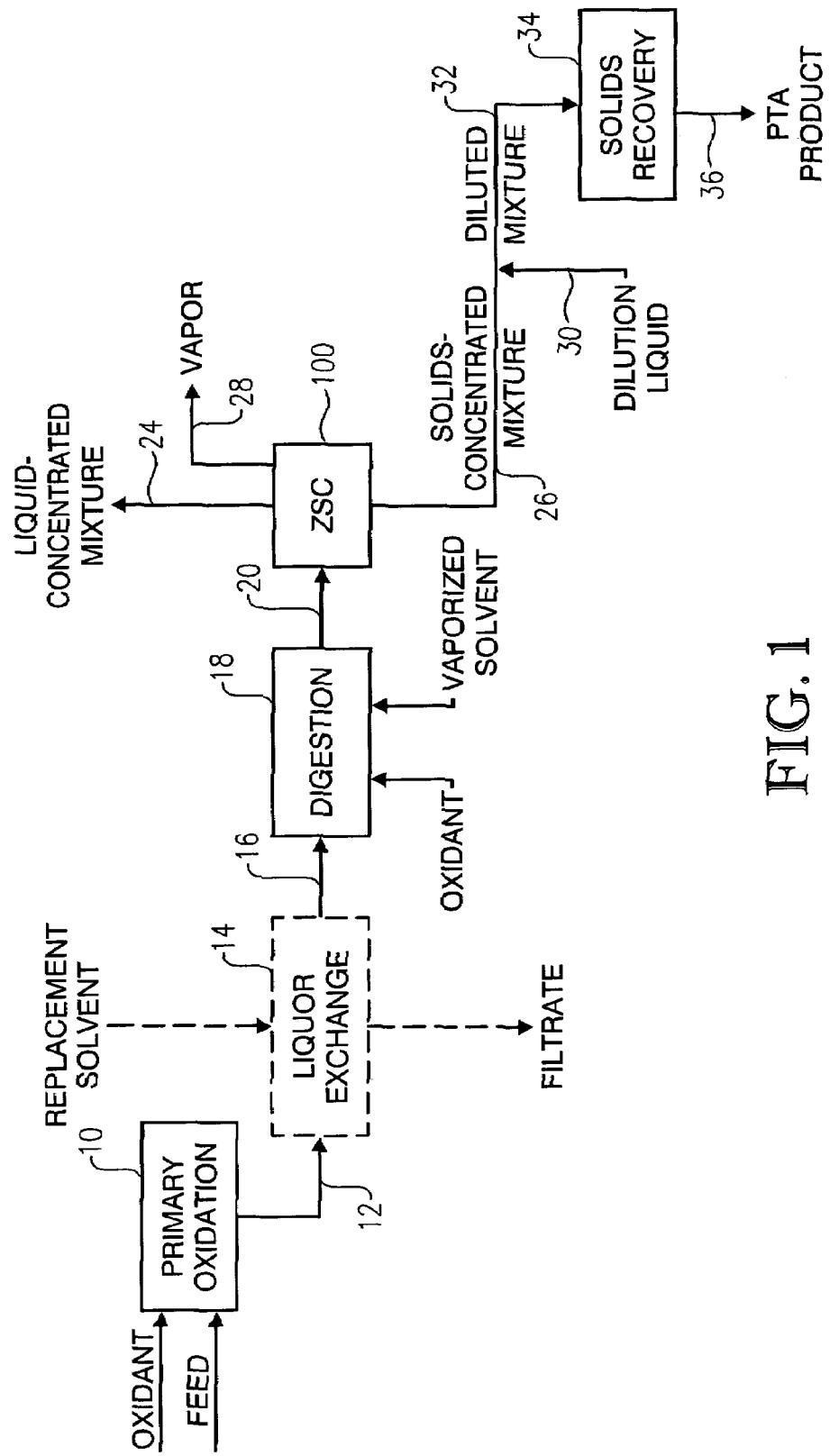
FIG. 1 is a process flow diagram illustrating a system for the production and purification of terephthalic acid constructed in accordance with a first embodiment of the present invention, particularly illustrating a configuration where the crude slurry from the primary oxidation reactor is subjected to oxidative digestion and the resulting slurry is subjected to combined crystallization and liquor exchange in a zoned slurry concentrator.

In the embodiment illustrated in FIG. 1, a predominately liquid-phase feed stream containing an oxidizable compound (e.g., para-xylene), a solvent (e.g., acetic acid+water), and a catalyst system (e.g., Co+Mn+Br) is introduced into a primary/initial oxidation reactor 10. A predominately gas-phase oxidant stream containing molecular oxygen is also introduced into primary oxidation reactor 10. The liquid- and gas-phase feed streams form a multi-phase reaction medium in oxidation reactor 10. The oxidizable compound undergoes partial oxidation in a liquid phase of the reaction medium contained in reactor 10.

Primary oxidation reactor 10 is preferably an agitated reactor. Agitation of the reaction medium in oxidation reactor 10 can be provided by any means known in the art. As used herein, the term "agitation" shall denote work dissipated into the reaction medium causing fluid flow and/or mixing. In one embodiment, primary oxidation reactor 10 is a mechanically-agitated reactor equipped with means for mechanically agitating the reaction medium. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. In a preferred embodiment of the invention, primary oxidation reactor 10 is a bubble column reactor. As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the terms "majority," "primarily," and "predominately" shall mean more than 50 percent.

The oxidizable compound present in the liquid-phase feed stream introduced into primary oxidation reactor 10 preferably comprises at least one hydrocarbyl group. More preferably, the oxidizable compound is an aromatic compound. Still more preferably, the oxidizable compound is an aromatic compound with at least one attached hydrocarbyl group or at least one attached substituted hydrocarbyl group or at least one attached heteroatom or at least one attached carboxylic acid function (—COOH). Even more preferably, the oxidizable compound is an aromatic compound with at least one attached hydrocarbyl group or at least one attached substituted hydrocarbyl group with each attached group comprising from 1 to 5 carbon atoms. Yet still more preferably, the oxidizable compound is an aromatic compound having exactly two attached groups with each attached group comprising exactly one carbon atom and consisting of methyl groups and/or substituted methyl groups and/or at most one carboxylic acid group. Even still more preferably, the oxidizable compound is para-xylene, meta-xylene, para-tolualdehyde, meta-tolualdehyde, para-toluic acid, meta-toluic acid, and/or acetaldehyde. Most preferably, the oxidizable compound is para-xylene.

A "hydrocarbyl group," as defined herein, is at least one carbon atom that is bonded only to hydrogen atoms or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. Aromatic compounds, as defined herein, comprise an aromatic ring, preferably having at least 6 carbon atoms, even more preferably having only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the liquid-phase feed stream introduced into primary oxidation reactor 10 is preferably in the range of from about 2 to about 40 weight percent, more preferably in the range of from about 4 to about 20 weight percent, and most preferably in the range of from 6 to 15 weight percent.

The solvent present in the liquid-phase feed stream introduced into primary oxidation reactor 10 preferably comprises an acid component and a water component. The solvent is preferably present in the liquid-phase feed stream at a concentration in the range of from about 60 to about 98 weight percent, more preferably in the range of from about 80 to about 96 weight percent, and most preferably in the range of from 85 to 94 weight percent. The acid component of the solvent is preferably an organic low molecular weight monocarboxylic acid having 1-6 carbon atoms, more preferably 2 carbon atoms. Most preferably, the acid component of the solvent is acetic acid. Preferably, the acid component makes up at least about 75 weight percent of the solvent, more preferably at least about 80 weight percent of the solvent, and most preferably in the range of from 85 to 98 weight percent of the solvent, with the balance being water.

The liquid-phase feed stream introduced into primary oxidation reactor 10 can also include a catalyst system. The catalyst system is preferably a homogeneous, liquid-phase catalyst system capable of promoting partial oxidation of the oxidizable compound. More preferably, the catalyst system comprises at least one multivalent transition metal. Still more preferably, the multivalent transition metal comprises cobalt. Even more preferably, the catalyst system comprises cobalt and bromine. Most preferably, the catalyst system comprises cobalt, bromine, and manganese.

When cobalt is present in the catalyst system, it is preferred for the amount of cobalt present in the liquid-phase feed stream to be such that the concentration of cobalt in the liquid phase of the reaction medium is maintained in the range of from about 300 to about 6,000 parts per million by weight (ppmw), more preferably in the range of from about 700 to about 4,200 ppmw, and most preferably in the range of from 1,200 to 3,000 ppmw. When bromine is present in the catalyst system, it is preferred for the amount of bromine present in the liquid-phase feed stream to be such that the concentration of bromine in the liquid phase of the reaction medium is maintained in the range of from about 300 to about 5,000 ppmw, more preferably in the range of from about 600 to about 4,000 ppmw, and most preferably in the range of from 900 to 3,000 ppmw. When manganese is present in the catalyst system, it is preferred for the amount of manganese present in the liquid-phase feed stream to be such that the concentration of manganese in the liquid phase of the reaction medium is maintained in the range of from about 20 to about 1,000 ppmw, more preferably in the range of from about 40 to about 500 ppmw, most preferably in the range of from 50 to 200 ppmw.

The weight ratio of cobalt to bromine (Co:Br) in the catalyst system introduced into primary oxidation reactor 10 is preferably in the range of from about 0.25:1 to about 4:1, more preferably in the range of from about 0.5:1 to about 3:1, and most preferably in the range of from 0.75:1 to 2:1. The weight ratio of cobalt to manganese (Co:Mn) in the catalyst system introduced is preferably in the range of from about 0.3:1 to about 40:1, more preferably in the range of from about 5:1 to about 30:1, and most preferably in the range of from 10:1 to 25:1.

During oxidation, it is preferred for the oxidizable compound (e.g., para-xylene) to be continuously introduced into primary oxidation reactor 10 at a rate of at least about 5,000 kilograms per hour, more preferably at a rate in the range of from about 10,000 to about 80,000 kilograms per hour, and most preferably in the range of from 20,000 to 50,000 kilograms per hour. During oxidation, it is preferred for the ratio of the mass flow rate of the solvent to the mass flow rate of the oxidizable compound entering oxidation reactor 10 to be maintained in the range of from about 2:1 to about 50:1, more preferably in the range of from about 5:1 to about 40:1, and most preferably in the range of from 7.5:1 to 25:1.

The predominately gas-phase oxidant stream introduced into primary oxidation reactor 10 preferably comprises in the range of from about 5 to about 40 mole percent molecular oxygen, more preferably in the range of from about 15 to about 30 mole percent molecular oxygen, and most preferably in the range of from 18 to 24 mole percent molecular oxygen. It is preferred for the balance of the oxidant stream to be comprised primarily of a gas or gases, such as nitrogen, that are inert to oxidation. More preferably, the oxidant stream consists essentially of molecular oxygen and nitrogen. Most preferably, the oxidant stream is dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in primary oxidation reactor 10, it is preferred for the oxidant stream to be introduced into reactor 10 in an amount that provides molecular oxygen somewhat exceeding the stoichiometric oxygen demand. Thus, it is preferred that the ratio of the mass flow rate of the oxidant stream (e.g., air) to the mass flow rate of the oxidizable compound (e.g., para-xylene) entering reactor 10 is maintained in the range of from about 0.5:1 to about 20:1, more preferably in the range of from about 1:1 to about 10:1, and most preferably in the range of from 2:1 to 6:1.

The liquid-phase oxidation reaction carried out in reactor 10 is preferably a precipitating reaction that generates solids. More preferably, the liquid-phase oxidation carried out in reactor 10 causes at least about 10 weight percent of the oxidizable compound (e.g., para-xylene) introduced into oxidation reactor 10 to form solids (e.g., CTA particles) in the reaction medium. Still more preferably, the liquid-phase oxidation causes at least about 50 weight percent of the oxidizable compound to form solids in the reaction medium. Most preferably, the liquid-phase oxidation causes at least 90 weight percent of the oxidizable compound to form solids in the reaction medium. It is preferred for the solids content of the reaction medium to be maintained in the range of from about 5 to about 40 weight percent, still more preferably in the range of from about 10 to about 35 weight percent, and most preferably in the range of from 15 to 30 weight percent. As used herein, the term "solids content" shall denote the weight percent solids in a multi-phase mixture.

During oxidation in oxidation reactor 10, the multi-phase reaction medium is preferably maintained at an elevated temperature in the range of from about 125 to about 200° C., more preferably in the range of from about 150 to about 180° C., and most preferably in the range of from 155 to 165° C. The overhead pressure in oxidation reactor 10 is preferably maintained in the range of from about 1 to about 20 bar gauge (barg), more preferably in the range of from about 2 to about 12 barg, and most preferably in the range of from 4 to 8 barg.

As illustrated in FIG. 1, a crude product slurry is withdrawn from an outlet of primary oxidation reactor 10 via line 12. The solid phase of the crude product slurry in line 12 is preferably formed primarily of solid particles of crude terephthalic acid (CTA). The liquid phase of the crude product slurry in line 12 is a liquid mother liquor comprising at least a portion of the solvent, the catalyst system, and minor amounts of dissolved TPA. The solids content of the crude product slurry in line 12 is preferably the same as the solids content of the reaction medium in primary oxidation reactor 10, discussed above. The crude product slurry in line 12 typically has a combined 4-carboxybenzaldehyde (4-CBA) and para-toluic acid (pTAc) content in a range of from about 100 to about 500 parts per million by weight (ppmw) based on the weight of the solids.

In one embodiment of the present invention, the crude product slurry in line 12 is transported directly (i.e., without intermediate processing steps) to a digester 18 for purification by oxidative digestion. In an alternative embodiment, an optional liquor exchange system 14 is employed to remove at least a portion of the liquid mother liquor from the crude product slurry and replace the removed mother liquor (i.e., filtrate) with a replacement solvent prior introduction into digester 18. The replacement solvent typically comprises acetic acid and/or water. The primary purpose of liquor exchange 14 is to provide cleaner solvent media for subsequent oxidative digestion of the CTA solids.

Optional liquor exchange system 14 can employ a variety of different apparatuses to remove and replace at least a portion of the crude mother liquor. For example, liquor exchange system 14 can employ a disc stack centrifuge to separate at least a portion of the mother liquor from the CTA solids and replace the removed mother liquor with a clean replacement solvent. Alternatively, liquor exchange can be accomplished using any suitable solid/liquid separator (e.g., a decanter centrifuge, a rotary disk centrifuge, a belt filter, or a rotary vacuum filter) and then diluting the resulting solids (typically a wet cake) with a clean replacement solvent. In one embodiment of the present invention, at least about 25 weight percent of the mother liquor in the crude product slurry is replaced with a replacement solvent, more preferably at least about 50 weight percent of the mother liquor is replaced with a replacement solvent, and most preferably in the range of from 75 to 99 weight percent of the mother liquor is replaced with a replacement solvent. When liquor exchange system 14 is employed, the resulting liquor-exchanged slurry is passed through line 16 to digester 18.

In digester 18, the crude product slurry or liquor-exchanged slurry is subjected to purification by oxidative digestion. As used herein, the term "oxidative digestion" denotes a process step or steps where a feed is subjected to oxidation. Digester 18 can be one or more reactors or zones. Preferably, digester 18 comprises one or more mechanically-agitated reactors. A secondary oxidant stream, which can have the same composition as the gas-phase oxidant stream fed to primary oxidation reactor 10, is introduced into digester 18 to provide the molecular oxygen required for oxidative digestion. Additional oxidation catalyst can also be added if necessary. As mentioned above, the crude product slurry or liquor-exchange slurry introduced into digester 18 contains significant quantities of impurities such as, for example, 4-CBA and p-TAc. The oxidative digestion in digester 18 preferably causes oxidation of a substantial portion of the 4-CBA and p-TAc to TPA.

The slurry fed to digester 18 typically has a 4-CBA content of at least about 100 parts per million based on the weight of the solids in the feed slurry ($ppmw_{fs}$), more typically in the range of from about 200 to about 10,000 $ppmw_{fs}$ and most typically in the range of from 800 to 5,000 $ppmw_{fs}$. The slurry fed to digester 18 typically has a p-TAc content of at least about 250 $ppmw_{fs}$, more typically in the range of from about 300 to about 5,000 $ppmw_{fs}$ and most typically in the range of from 400 to 1,500 $ppmw_{fs}$. The slurry product exiting digester 18 preferably has a 4-CBA content of less than about 150 parts per million based on the weight of the solids in the product slurry ($ppmw_{ps}$), more preferably less than about 100 $ppmw_{ps}$, and most preferably less than 50 $ppmw_{ps}$. The slurry product exiting digester 18 preferably has a p-TAc content of less than about 300 $ppmw_{ps}$, more preferably less than about 200 $ppmw_{ps}$ and most preferably less than 150 $ppmw_{ps}$. Preferably, oxidative digestion in digester 18 causes the product slurry exiting digester 18 to have 4-CBA and/or p-TAc content that is at least about 50 percent less than the 4-CBA and/or p-TAc content of the slurry fed to digester 18, more preferably at least about 85 percent less, and most preferably at least 95 percent less. By way of illustration, if the 4-CBA content of the slurry fed to digester 18 is 200 $ppmw_{fs}$ and the 4-CBA content of the product slurry exiting digester 18 is 100 $ppmw_{ps}$, then the 4-CBA content of the product slurry is 50 percent less than the 4-CBA content of the feed slurry.

The temperature at which oxidative digestion is carried out in digester 18 is preferably at least about 110° C. greater than the temperature of oxidation in primary oxidation reactor 10, more preferably in the range of from about 20 to about 80° C. greater, and most preferably in the range of from 30 to 50° C. greater. The additional heat required for the operation of digester 18 may be provided by supplying a vaporized solvent to digester 18 and allowing the vaporized solvent to condense therein. The oxidative digestion temperature in digester 18 is preferably maintained in the range of from about 180 to about 240° C., more preferably in the range of from about 190 to about 220° C., and most preferably in the range of from 200 to 210° C. The oxidative digestion pressure in digester 18 is preferably maintained in the range of from about 100 to about 350 pounds per square inch gauge (psig), more preferably in the range of from about 175 to about 275 psig, and most preferably in the range of from 185 to 225 psig.

In one embodiment of the present invention, digester 18 includes two digestion reactors/zones—an initial digester and a final digester. When digester 18 includes an initial digester and a final digester, it is preferred for the final digester to be operated at a lower temperature and pressure than the initial digester. Preferably, the operating temperature of the final digester is at least about 2° C. lower than the operating temperature of the initial digester. Most preferably, the operating temperature of the final digester is in the range of from about 5 to about 15° C. lower than the operating temperature of the initial digester. Preferably, the operating pressure of the final digester is at least about 5 psi lower than the operating pressure of the initial digester. Most preferably, the operating pressure of the final digester is in the range of from about 10 to about 50 psig lower than the operating temperature of the initial digester. Preferably, the operating temperature of the initial digester is in the range of from about 195 to about 225° C., more preferably in the range of from 205 to 215° C., and most preferably about 210° C. Preferably, the operating pressure of the initial digester is in the range of from about 215 to 235 psig, most preferably about 225 psig. Preferably, the operating temperature of the final digester is in the range of from about 190 to about 220° C., more preferably in the range of from 200 to 210° C., and most preferably about 205° C. Preferably, the operating pressure of the final digester is in the range of from about 190 to 210 psig, most preferably about 200 psig.

Referring again to FIG. 1, an oxidation-treated slurry is discharged from digester 18 via line 20. The solid phase of the oxidation-treated slurry is formed primarily of purified terephthalic acid (PTA) particles, while the liquid phase is formed of an oxidation-treated mother liquor. The solids content of the oxidation-treated slurry in line 20 is preferably in the range of from about 1 to about 50 percent by weight, more preferably in the range of from about 5 to about 40 percent by weight, and most preferably in the range of from 20 to 30 percent by weight. The oxidation-treated slurry in line 20 is introduced into a zoned slurry concentrator 100.

As used herein, the term "zoned slurry concentrator" means a single vessel having at least one internal upright baffle that divides at least a portion of the vessel's internal volume into an agitated zone and a settling zone; where the agitated zone communicates with the settling zone proximate a lower end/opening of the lowest baffle; and where the vessel defines a liquids outlet for removing a liquid-concentrated mixture from the settling zone at an elevation above the lower end/opening of the lowest baffle and a solids outlet for removing a solids-concentrated mixture from the vessel at an elevation below the liquids outlet.

Figure 2:
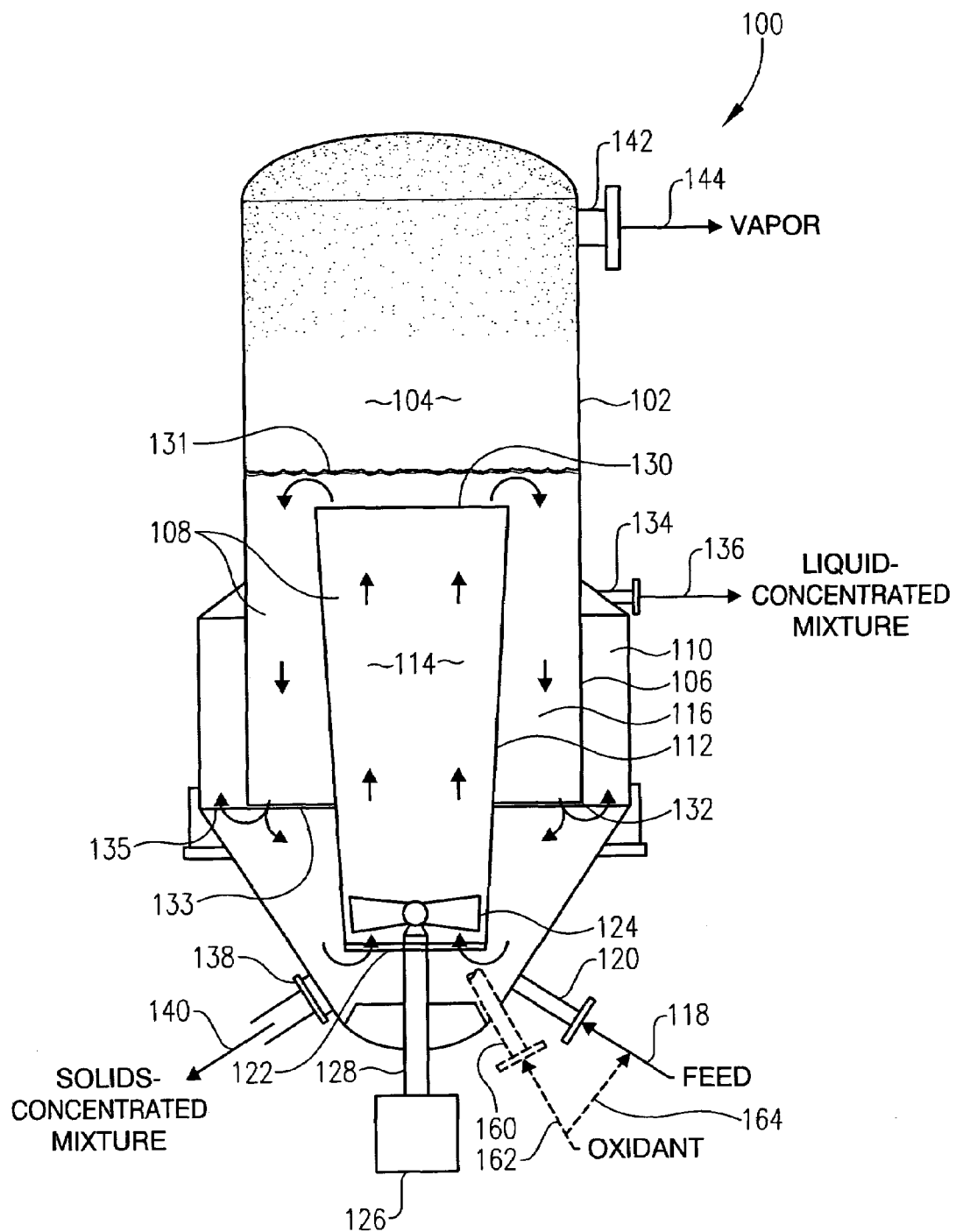
FIG. 2 is a schematic representation of a zoned slurry concentrator having an agitated zone and a settling zone, where a liquid-concentrated mixture is withdrawn near the top of the settling zone and a solids-concentrated mixture is withdrawn a substantial distance below the top of the settling zone.

FIG. 2 illustrates a preferred zoned slurry concentrator 100 suitable for use in the present invention. Zoned slurry concentrator 100 comprises a vessel shell 102 that defines and internal volume 104. Vessel shell 102 preferably has at least one substantially vertical sidewall that has a generally cylindrical and/or frustoconical configuration. Zoned slurry concentrator 100 also comprises at least one upright baffle 106 that separates at least a portion of internal volume 104 into an agitated zone 108 and a settling zone 110. Upright baffle 106 can be formed of a single member, or a plurality of baffle members. Upright baffle 106 preferably includes at least one generally cylindrical and/or frustoconical baffle spaced inwardly from the upright sidewalls of vessel shell 102. Zoned slurry concentrator 100 also comprises an upright draft tube 112 at least partly disposed in agitated zone 108. Draft tube 112 is preferably a substantially hollow, generally cylindrical or frustoconical tube spaced inwardly from upright baffle 106. An upwardly moving section 114 of agitated zone 108 is defined within draft tube 112, and a downwardly moving section 116 of agitated zone 108 is defined between draft tube 112 and vessel shell 102.

In operation, a feed slurry in line 118 is introduced into zoned slurry concentrator 100 via a feed inlet 120. The feed slurry enters a lower opening 122 of draft tube 112 and is forced upwardly by a rotating propeller 124. Propeller 124 is powered by a motor 126. Motor 126 and propeller 124 are connected by a drive shaft 128 that extends through vessel shell 102 and into agitated zone 108 of internal volume 104. The feed slurry moves upwardly though draft tube 112 and then exits an upper opening 130 of draft tube 112. The level of slurry in vessel shell 102 is maintained so that the upper surface 131 of the slurry is above upper opening 130 of draft tube 112. As the slurry exits upper opening 130 of draft tube 112, it circulates into a downward flow pattern in downwardly-moving section 116 of agitated zone 108. At least a portion of downwardly-moving section 116 of agitated zone 108 is defined between draft tube 112 and upright baffle 106. An agitated zone outlet opening 133 is defined between baffle 106 and draft tube 112 proximate the bottom of upright baffle 106. The slurry exits agitated zone 108 through agitated zone outlet opening 133. The after exiting agitated zone 108 the slurry enter settling zone 110 via a settling zone opening 135. Settling zone opening 135 is defined between vessel shell 102 and baffle 106 proximate the bottom of upright baffle 106.

Upright baffle 106 is operable to substantially isolate settling zone 110 from the turbulence generated by rotating propeller in agitated zone 108. In settling zone 110, the liquid phase of the slurry moves upwardly in a relatively non-turbulent manner at a velocity less than the velocity necessary to suspend the solid phase in the upwardly moving liquid phase. This relatively slow, non-turbulent, upward flow of the liquid phase in settling zone 110 permits the downward gravitational force acting on the solid phase particles to overcome the upward liquid flow forces acting on the solid phase particles, thereby cause solid/liquid disengagement in settling zone 110. This solid/liquid disengagement in settling zone 110 produces a liquid-concentrated mixture with low solids content from the top of settling zone 110. The liquid-concentrated mixture is withdrawn from internal volume 104 via liquids outlet 134 and is transported away from zoned slurry concentrator 100 in line 136. The solid particles that travel downward through settling zone 110 exit settling zone 110 via settling zone opening 135. These solids accumulate near the bottom of internal volume 104 of vessel shell 102, thereby forming a solids-concentrated mixture with high solids content. The solids-concentrated mixture is withdrawn from internal volume 104 via solids outlet 138 and is transported away from zoned slurry concentrator 100 in line 140. Vapor introduced into or formed in zoned slurry concentrator 100 is discharged through a vapor outlet 142 and transported away from zoned slurry concentrator 100 in line 144.

In a preferred embodiment of the present invention, the feed slurry introduced into zoned slurry concentrator 100 via feed inlet 120 has a solids content in the range of from about 1 to about 50 weight percent, more preferably in the range of from about 5 to about 40 weight percent, and most preferably in the range of from 20 to 30 weight percent. It is preferred for the solids in the feed slurry introduced into zoned slurry concentrator 100 to be formed of at least about 75 weight percent TPA, more preferably at least about 90 weight percent TPA, and most preferably at least 95 weight percent TPA.

The solids-concentrated mixture exiting zoned slurry concentrator 100 via solids outlet 138 preferably has a solids content of more than about 60 weight percent, more preferably more than about 80 weight percent, and most preferably more than 95 weight percent. The liquid-concentrated mixture exiting zoned slurry concentrator 100 via liquids outlet 134 preferably has a solids content of less than about 40 weight percent, more preferably less than about 20 weight percent, and most preferably less than 5 weight percent.

Preferably, the solids content of the liquid-concentrated mixture exiting zoned slurry concentrator 100 via liquids outlet 134 is at least about 50 percent less than the solids content of the feed slurry, more preferably at least about 75 percent less than the solids content of the feed slurry, and most preferably at least 90 percent less than the solids content of the feed slurry. For example, if the feed slurry has a solids content of 30 weight percent and the liquid-concentrated mixture has a solids content of 15 weight percent, then the liquid-concentrated mixture has a solids content that is 50 percent less than the solids content of the feed slurry. Preferably, the solids content of the solids-concentrated mixture exiting zoned slurry concentrator 100 via solids outlet 138 is at least about 50 percent greater than the solids content of the feed slurry, more preferably at least about 100 percent greater than the solids content of the feed slurry, and most preferably at least 200 percent greater than the solids content of the feed slurry. For example, if the feed slurry has a solids content of 30 weight percent and the solids-concentrated mixture has a solids content of 45 weight percent, then the solids-concentrated mixture has a solids content that is 50 percent greater than the solids content of the feed slurry.

The ratio of the solids content of the solids-concentrated mixture exiting zoned slurry concentrator 100 via solids outlet 138 to the liquid-concentrated mixture exiting zoned slurry concentrator 100 via liquids outlet 134 is preferably at least about 2:1, more preferably at least about 10:1, and most preferably at least 50:1. The ratio of the solids content of the solids-concentrated mixture exiting zoned slurry concentrator 100 via solids outlet 138 to the feed slurry entering zoned slurry concentrator 100 via feed inlet 120 is preferably at least about 1.5:1, more preferably at least about 5:1, and most preferably at least 25:1. The ratio of the solids content of the feed slurry entering zoned slurry concentrator 100 via feed inlet 120 to the liquid-concentrated mixture exiting zoned slurry concentrator 100 via liquids outlet 134 is preferably at least about 1.5:1, more preferably at least about 5:1, and most preferably at least 25:1.

In one embodiment of the present invention, the solids-concentrated mixture is diluted with a dilution liquid. This dilution of the solids-concentrated mixture can be accomplished by introducing the dilution liquid into zoned slurry concentrator 100 at a location near solids outlet 138. Preferably, dilution is accomplished by introducing the dilution liquid into the solids-concentrated mixture after the solids-concentrated mixture has been removed from zoned slurry concentrator 100. The dilution liquid can function as a "clean" replacement solvent for the solvent removed from zoned slurry concentrator 100 with the liquid-concentrated mixture. The dilution liquid is preferably a solvent for TPA. Most preferably, the dilution liquid comprises acetic acid and/or water.

Dilution of the solids-concentrated mixture with the dilution liquid forms a diluted mixture. Preferably, the dilution liquid is added to the solids-concentrated mixture in an amount such that the solids content of the diluted mixture is at least about 25 percent less than the solids content of the solids-concentrated mixture, more preferably at least about 50 percent less of the solids content of the solids-concentrated mixture, and most preferably in the range of from 60 to 90 percent less than the solids content of the solids-concentrated mixture. Preferably, the solids content of the diluted mixture is in the range of from about 1 to about 50 weight percent, more preferably in the range of from about 5 to about 40 weight percent, and most preferably in the range of from 20 to 30 weight percent.

Figure 3:
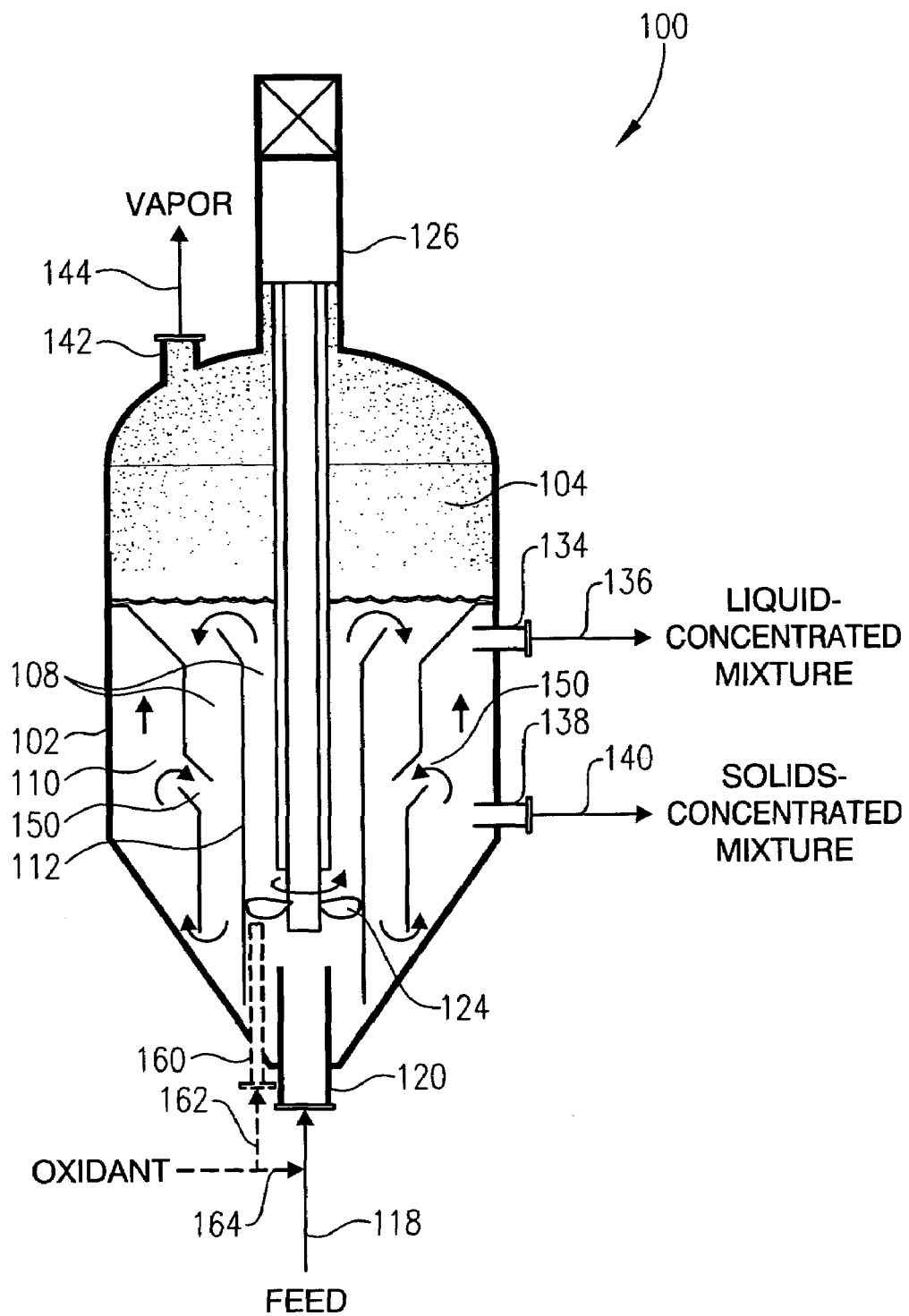
FIG. 3 is a schematic representation of an alternative zoned slurry concentrator, where the liquid-concentrated mixture is withdrawn near the top of the settling zone and the solids-concentrated is withdrawn near the bottom of the settling zone.

FIG. 3 illustrates an alternative embodiment of zoned slurry concentrator 100. Common components of the zoned slurry concentrators illustrated in FIGS. 2 and 3 are identified with common reference numerals. One difference between the zoned slurry concentrators of FIGS. 2 and 3 is that upright baffle 106 of the zoned slurry concentrator illustrated in FIG. 3 includes one or more circulation openings 150 between the upper and lower ends of upright baffle 106. Another difference between the zoned slurry concentrators of FIGS. 2 and 3 is that solids outlet 138 of the zoned slurry concentrator 100 illustrated in FIG. 3 withdraws the solids-concentrated mixture at a higher point than solids outlet 138 of FIG. 2.

FIGS. 2 and 3 illustrate specific embodiments of zoned slurry concentrators suitable for use in the present invention. It should be noted, however, that devices having significantly different configurations than those illustrated in FIGS. 2 and 3 may also fall within the definition of "zoned slurry concentrator," provided herein. One example of a commercially-available zoned slurry concentrator suitable for use in the present invention is a "Draft Tube Baffle (DTB) Crystallizer," available from Swenson Technology, Inc., Monee, Ill.

In the embodiment illustrated in FIG. 1, feed line 20 is equivalent to feed line 118 of FIG. 2, liquids line 24 is equivalent to liquids line 136 of FIG. 2, and solids line 26 is equivalent to solids line 140 of FIG. 2. The system shown in FIG. 1 employs zoned slurry concentrator 100 as a post-digestion crystallizer. Post-digestion crystallization is preferably carried out at a temperature and pressure lower than the temperature and pressure of the final oxidative digestion performed in digester 18. Preferably, the post-digestion crystallization temperature is at least about 10° C. less than the final digestion temperature, more preferably in the range of from about 15 to about 65° C. less than the final digestion temperature, and most preferably in the range of from 25 to 55° C. less than the final digestion temperature. Preferably, the post-digestion crystallization temperature is maintained in the range of from about 130 to about 200° C., more preferably in the range of from about 150 to about 180° C., and most preferably in the range of from 160 to 170° C. Preferably the post-digestion crystallization pressure is maintained in the range of from about 10 to about 150 psig, more preferably in the range of from about 50 to about 120 psig, and most preferably about 80 psig.

Referring again to FIG. 1, the solids-concentrated mixture exiting zoned slurry concentrator 100 via line 26 can be diluted with a dilution liquid supplied via line 30. As discussed above, in one embodiment of the present invention, the dilution liquid is combined with the solids-concentrated mixture in an external dilution zone located outside of zoned slurry concentrator 100. In another embodiment of the invention, the dilution liquid is combined with the solids-concentrated mixture in an internal dilution zone located inside zoned slurry concentrator 100. The amount and composition of the dilution liquid introduced into the solids-concentrated mixture is discussed above with reference to FIG. 2.

The diluted mixture resulting from dilution of the solids-concentrated mixture with the dilution liquid is transported in line 32 to a solids recovery system 34 for recovery of solid PTA particles. Solids recovery system 34 preferably includes at least one solid/liquid separator and at least one drier. The solid/liquid separator employed as part of solids recovery system 34 can be any conventional solid/liquid separator such as, for example, a decanter centrifuge, a rotary disk centrifuge, a belt filter, or a rotary vacuum filter. The solids separated in the solid/liquid separator can then be dried using any suitable drier known in the art. The recovered, dried PTA solids are discharged from solids recovery system 34 via line 36.

Figure 4:
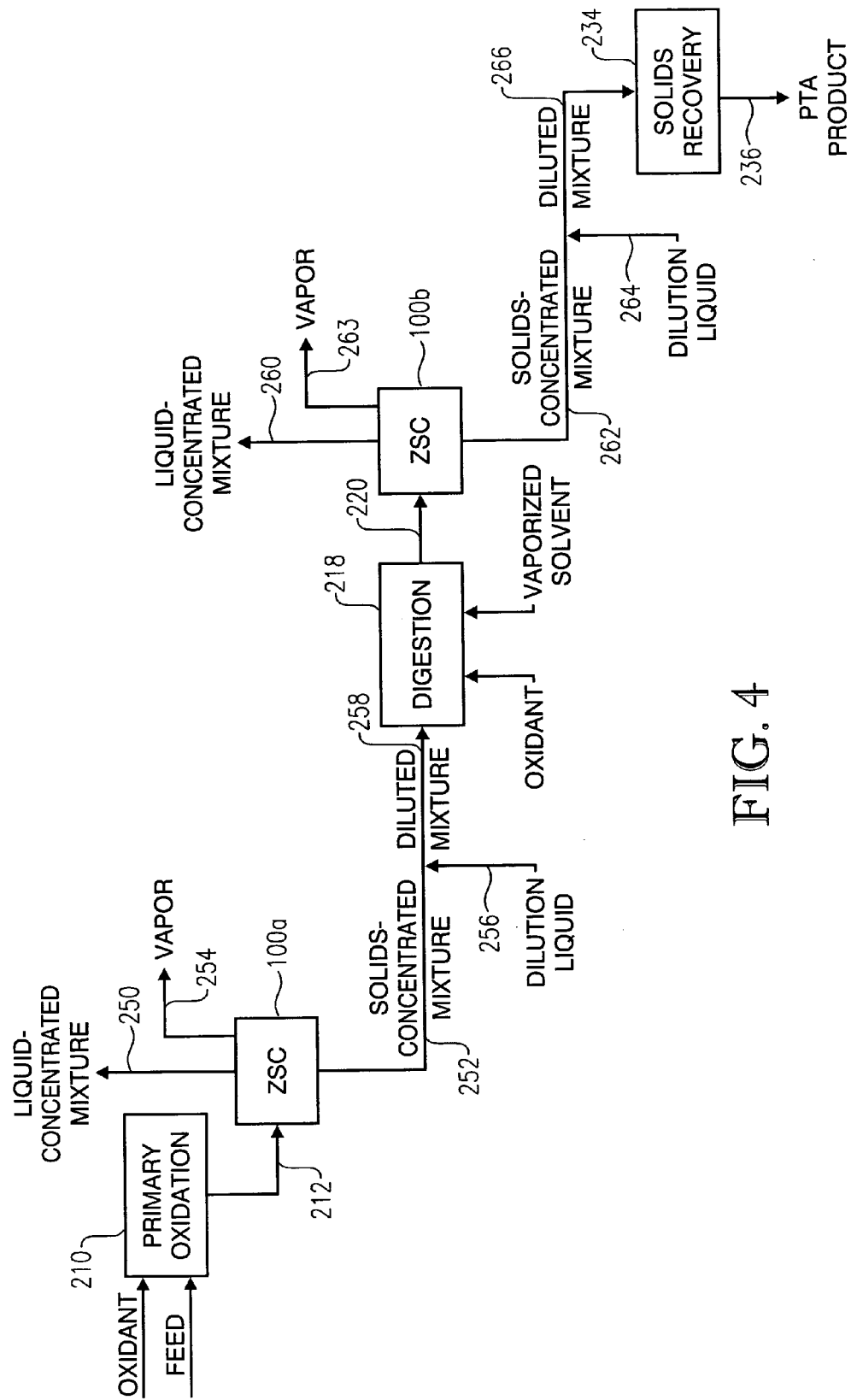
FIG. 4 is a process flow diagram illustrating a system for the production and purification of terephthalic acid constructed in accordance with a second embodiment of the present invention, particularly illustrating a configuration where the crude slurry exiting the primary oxidation reactor is subjected to combined crystallization and liquor exchange in a zoned slurry concentrator prior to oxidative digestion, and the slurry exiting the digester is also subjected to combined crystallization and liquor exchange prior to solids recovery.

FIG. 4 illustrates an embodiment of the present invention where two zoned slurry concentrators 100a and 100b are employed to aid in the purification of the crude oxidation product from primary oxidation reactor 210. In the embodiment of FIG. 4, primary oxidation reactor 210, digester 218, and solids recovery system 234 are operated in substantially the same manner as discussed above with reference to primary oxidation reactor 10, digester 18, and solids recovery system 34 of FIG. 1. However, the system of FIG. 4 employs zoned slurry concentrator 100a to perform liquor exchange and/or crystallization between primary oxidation reactor 210 and digester 218. Further, the system of FIG. 4 employs zoned slurry concentrator 100b to perform crystallization and/or liquor exchange between digester 218 and solids recovery system 234.

Zoned slurry concentrator 100a receives the crude product slurry directly from primary oxidation reactor 210 via line 212. In zoned slurry concentrator 100a, the crude product slurry is separated into a liquid-concentrated mixture exiting via line 250 and a solids-concentrated mixture exiting via line 252. Further, vapor exits zoned slurry concentrator 100a via line 254. In the embodiment illustrated in FIG. 4, line 212 is equivalent to line 118 of FIG. 2, line 250 is equivalent to line 136 of FIG. 2, line 252 is equivalent to line 140 of FIG. 2, and line 254 is equivalent to line 144 of FIG. 2. Zoned slurry concentrator 100a of FIG. 4 preferably operates in substantially the same manner described above with reference to the zoned slurry concentrators of FIGS. 2 and 3.

The solids-concentrated mixture exiting zone slurry concentrator 100a via line 252 is diluted with a dilution liquid in line 256. This dilution liquid is preferably a clean replacement solvent that replaces the crude mother liquor removed from zoned slurry concentrator 100a via line 250. The amount and composition of dilution liquid used to dilute the solids-concentrated mixture is described above with reference to FIG. 2. The resulting diluted mixture is introduced into digester 218 via line 258 for purification by oxidative digestion.

The oxidation-treated slurry exits digester 218 via line 220 and is introduced into zoned slurry concentrator 100b. In zoned slurry concentrator 100b, the oxidation-treated slurry is separated into a liquid-concentrated mixture exiting via line 260 and a solids-concentrated mixture exiting via line 262. Further, vapor exits zoned slurry concentrator 100b via line 263. In the embodiment illustrated in FIG. 4, line 220 is equivalent to line 118 of FIG. 2, line 260 is equivalent to line 136 of FIG. 2, line 262 is equivalent to line 140 of FIG. 2, and line 263 is equivalent to line 144 of FIG. 2. Zoned slurry concentrator 100b of FIG. 4 preferably operates in substantially the same manner described above with reference to the zoned slurry concentrators of FIGS. 2 and 3.

The solids-concentrated mixture exiting zone slurry concentrator 100b via line 162 is diluted with a dilution liquid in line 264. This dilution liquid is preferably a clean replacement solvent that replaces the oxidation-treated mother liquor removed from zoned slurry concentrator 100b via line 260. The amount and composition of dilution liquid used to dilute the solids-concentrated mixture is described above with reference to FIG. 2. The resulting diluted mixture is introduced into solids recovery system 234 via line 266 for recovery of PTA solids.

Figure 5:
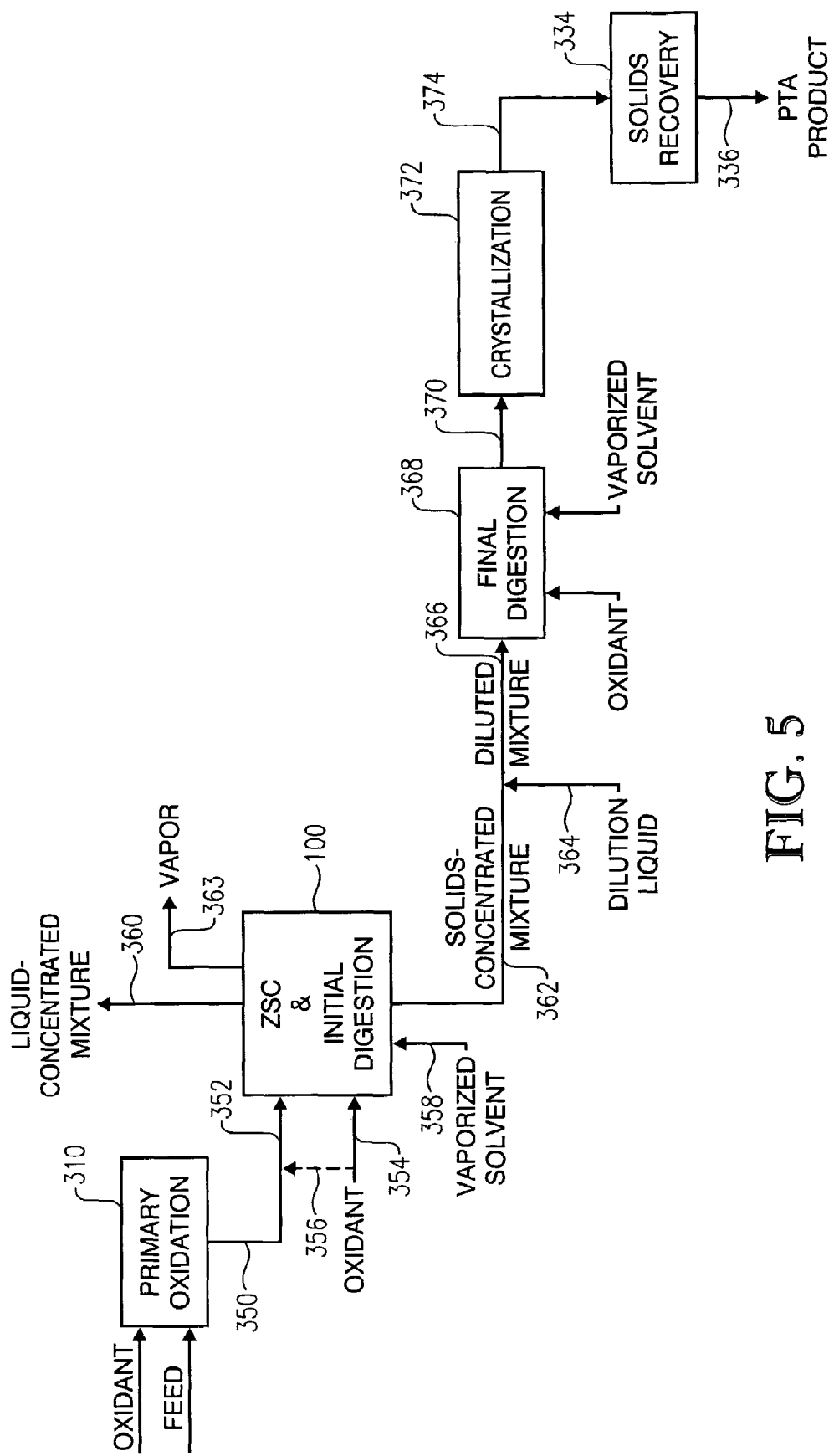
FIG. 5 is a process flow diagram illustrating a system for the production and purification of terephthalic acid constructed in accordance with a third embodiment of the present invention, particularly illustrating a configuration where the crude slurry exiting the primary oxidation reactor is subjected to combined oxidative digestion and liquor exchange in a zoned slurry concentrator, followed by final oxidative digestion, crystallization, and solids recovery steps.

FIG. 5 illustrates an embodiment of the present invention where zoned slurry concentrator 100 is employed as the initial digester in a process that includes purification by two-step oxidative digestion. In the embodiment of FIG. 5, primary oxidation reactor 310 and solids recovery system 334 operate in substantially the same manner as discussed above with reference to primary oxidation reactor 10 and solids recovery system 34 of FIG. 1. However, the system of FIG. 5 employs zoned slurry concentrator 100 to perform initial oxidative digestion, liquor exchange, and/or crystallization of the crude product slurry exiting primary oxidation reactor 310 via line 350. Further, the system of FIG. 5 employs a final digester 368 for providing further oxidative digestion of the solids exiting zoned slurry concentrator 100. Finally, the system of FIG. 5 employs a crystallization system 372 downstream of final digester 368 and upstream of solids recovery system 334.

Zoned slurry concentrator 100 receives the crude product slurry directly from primary oxidation reactor 310. In order for oxidative digestion to be carried out in zoned slurry concentrator 100, an oxidant stream containing molecular oxygen is introduced into zoned slurry concentrator 100 via line 354. Alternatively, the oxidant stream can be introduced into the crude product slurry upstream of zoned slurry concentrator 100 via line 356, thereby providing an oxygen-enriched crude slurry in line 352. As illustrated in FIGS. 2 and 3, when the oxidant stream is introduced into zoned slurry concentrator 100, an additional oxidant inlet 160 is provided in zoned slurry concentrator 100 for receiving the oxidant stream. Oxidant inlet 160 preferably discharges the oxidant stream at a location just below the propeller 124. In the embodiment illustrated in FIG. 5, line 354 is equivalent to line 162 of FIGS. 2 and 3, while line 356 is equivalent to line 164 of FIGS. 2 and 3.

Initial oxidative digestion is carried out in zoned slurry concentrator 100 in a manner and under conditions that are substantially similar to the initial oxidative digestion described above. The initial digested solids-concentrated mixture exiting zoned slurry concentrator 100 via line 362 is diluted with a dilution liquid in line 364 to thereby produce a diluted mixture introduced into final digester 368 via line 366. Final oxidative digestion is carried out in final digester 368 in the manner previously described. The final digested slurry exiting final digester 368 is introduced into crystallization system 372 via line 370. In crystallization system 372, solids precipitate due to reduced temperature and pressure—typically in a series of crystallization zones. Typically, the temperature in crystallization system 372 is maintained in the range of from about 30 to about 190° C. The crystallized slurry produced in crystallization system 372 is transported to solids recovery system 334 via line 374 for recovery of the final PTA product.

Figure 6:
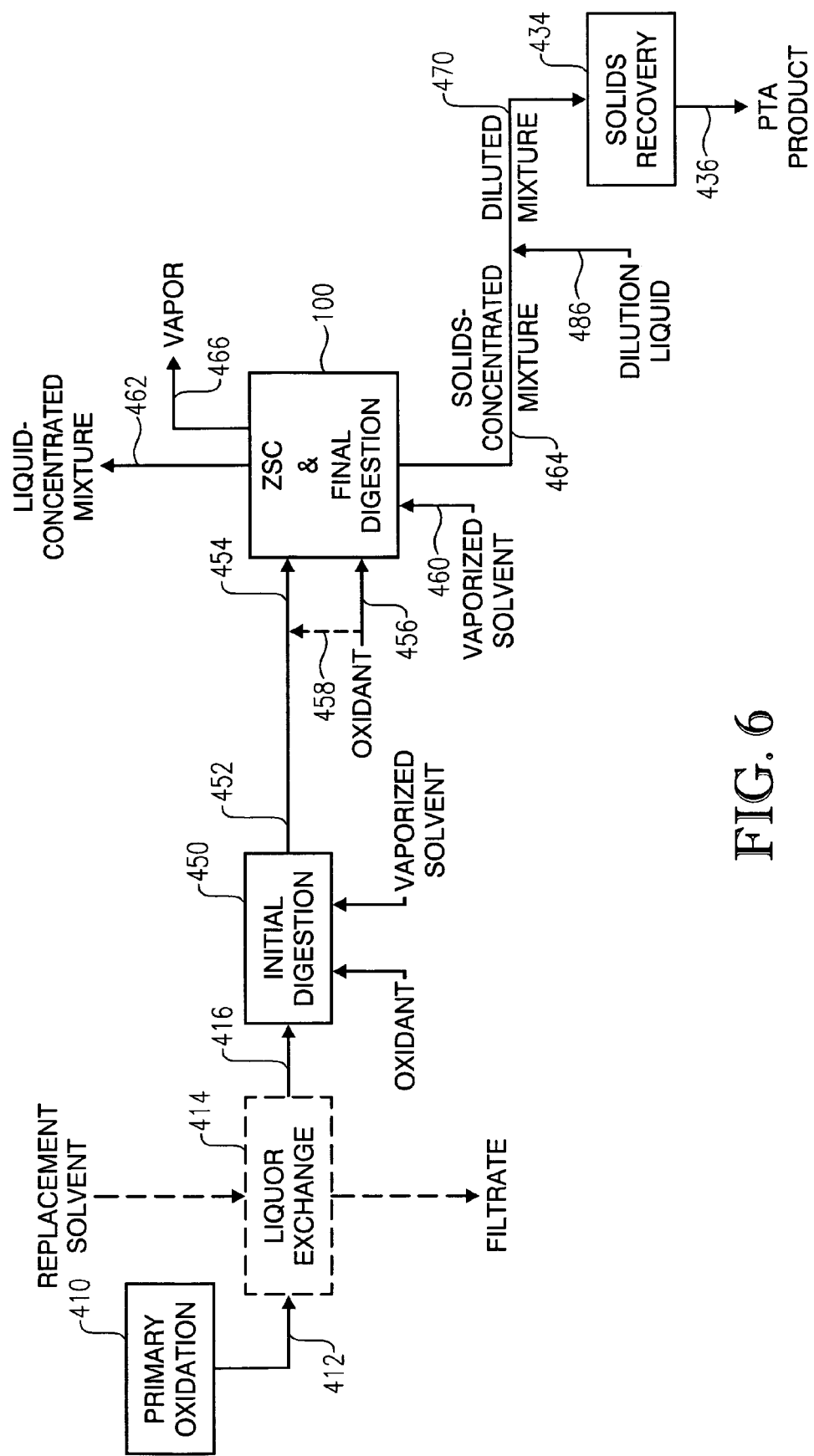
FIG. 6 is a process flow diagram illustrating a system for the production and purification of terephthalic acid constructed in accordance with a fourth embodiment of the present invention, particularly illustrating a configuration where the crude slurry exiting the primary oxidation reactor is subjected to initial oxidative digestion in a conventional reactor, followed by combined oxidative digestion and liquor exchange in a zone slurry concentrator.

FIG. 6 illustrates an embodiment of the present invention where zoned slurry concentrator 100 is employed as the final digester in a process that includes purification by two-step oxidative digestion. In the embodiment of FIG. 6, primary oxidation reactor 410, liquor exchange system 414, and solids recovery system 434 operate in substantially the same manner as discussed above with reference to primary oxidation reactor 10, liquor exchange system 14, and solids recovery system 34 of FIG. 1. However, the system of FIG. 6 employs zoned slurry concentrator 100 to perform final oxidative digestion, liquor exchange, and/or crystallization of the initial digested slurry exiting initial digester 450 via line 452.

The crude product slurry or liquor-exchanged slurry produced from primary oxidation reactor 410 or liquor exchange system 414 (depending on whether or not liquor exchange system 414 is employed) is introduced into initial digester 450 for initial oxidative digestion. The oxidative digestion in initial digester 450 is carried out in accordance with the previous description. The resulting initial digested slurry exits initial digester 450 via line 452 and is introduced into zoned slurry concentrator 100 for final oxidative digestion.

In order for oxidative digestion to be carried out in zoned slurry concentrator 100, an oxidant stream containing molecular oxygen is introduced into zoned slurry concentrator 100 via line 456. Alternatively, the oxidant stream can be introduced into the initial digested slurry upstream of zoned slurry concentrator 100 via line 458, thereby providing an oxygen-enriched slurry in line 454. As illustrated in FIGS. 2 and 3, when the oxidant stream is introduced into zoned slurry concentrator 100, an additional oxidant inlet 160 is provided in zoned slurry concentrator 100 for receiving the oxidant stream. In the embodiment illustrated in FIG. 6, line 456 is equivalent to line 162 of FIGS. 2 and 3, while line 458 is equivalent to line 164 of FIGS. 2 and 3.

Final oxidative digestion is carried out in zoned slurry concentrator 100 in a manner and under conditions that are substantially similar to the final oxidative digestion described above. The final digested solids-concentrated mixture exiting zoned slurry concentrator 100 via line 464 is diluted with a dilution liquid in line 486 to thereby produce a diluted mixture. The diluted mixture is transported to solids recovery system 434 via line 470 for recovery of the final PTA product.

The inventors note that for all numerical ranges provided herein, the upper and lower ends of the ranges can be independent of one another. For example, a numerical range of 10 to 100 means greater than 10 and/or less than 100. Thus, a range of 10 to 100 provides support for a claim limitation of greater than 10 (without the upper bound), a claim limitation of less than 100 (without the lower bound), as well as the full 10 to 100 range (with both upper and lower bounds).

The inventors also note that, as used herein, "coupled in communication" denotes a direct or indirect connection that permits the flow of solids and/or liquids. For example, the outlet of primary oxidation reactor 10 (FIG. 1) is "coupled in communication" with the inlet of zoned slurry concentrator 100, even though there is intermediate equipment (e.g., digester 18) located therebetween.

The invention has been described in detail with particular reference to preferred embodiments thereof, but will be understood that variations and modification can be affected within the spirit and scope of the invention.

We claim:
1. A process comprising:
   (a) oxidizing one or more reactants in a primary oxidation reactor to thereby produce a solid/liquid mixture comprising crude terephthalic acid (CTA) particles; and
   (b) simultaneously subjecting at least a portion of said solid/liquid mixture to oxidative digestion and concentration in a zoned slurry concentrator, said zoned slurry concentrator comprising a single vessel having an agitated zone and a settling zone, wherein the vessel defines a liquid outlet for removing a liquid-concentrated mixture and a solids outlet for removing a solids-concentrated mixture, thereby producing a solids-concentrated mixture containing oxidation-treated terephthalic acid (TPA) particles.

2. The process of claim 1 wherein at least a portion of said solid/liquid mixture is transported directly from said primary oxidation reactor to said zoned slurry concentrator without intermediate processing steps.

3. The process of claim 1 wherein at least a portion of said solid/liquid mixture is subjected to at least one intermediate processing step prior to introduction into said zoned slurry concentrator.

4. The process of claim 3 wherein said at least one intermediate processing step includes one or more of the following steps: (i) solid/liquid separation; (ii) partial liquid replacement; (iii) full liquid replacement; and (iv) oxidative digestion.

5. The process of claim 1 wherein said process includes subjecting at least a portion of said solid/liquid mixture to oxidative digestion in an initial digester to thereby produce an initial oxidation-treated mixture, wherein at least a portion of said initial oxidation-treated mixture is subjected to said oxidative digestion of step (b).

6. The process of claim 1 wherein said process includes subjecting at least a portion of said solids-concentrated mixture to oxidative digestion in a final digester.

7. The process of claim 1 wherein said process includes introducing an oxidant stream comprising molecular oxygen into said zoned slurry concentrator.

8. The process of claim 1 wherein said process includes introducing an oxidant stream comprising molecular oxygen into at least a portion of said solid/liquid mixture at a location upstream of said zoned slurry concentrator.

9. The process of claim 1 wherein said subjecting of step (b) includes introducing a feed slurry into said zoned slurry concentrator, wherein said feed slurry comprises at least a portion of said solid/liquid mixture, wherein said process includes producing a liquid-concentrated mixture from said zoned slurry concentrator, wherein said liquid-concentrated mixture has a lower solids content than said feed slurry, wherein said solids-concentrated mixture has a higher solids content than said feed slurry.

10. The process of claim 9 wherein said solids-concentrated mixture has a solids content that is at least about 50 percent greater than the solids content of said feed slurry, wherein said liquid-concentrated mixture has a solids content that is at least about 50 percent less than the solids content of said feed slurry.

11. The process of claim 9 wherein the solids content of said feed slurry is in the range of from about 1 to about 50 percent by weight, wherein the solids content of said solids-concentrated mixture is at least about 80 percent by weight, wherein the solids content of said liquid-concentrated mixture is less than about 20 percent by weight.

12. The process of claim 1 wherein said process includes combining a dilution liquid with said solids-concentrated mixture to thereby produce a diluted mixture.

13. The process of claim 12 wherein said process includes recovering TPA-containing solids from at least a portion of said diluted mixture.

14. The process of claim 1 wherein the 4-carboxybenzaldehyde (4-CBA) content of said solids-concentrated mixture, based on the weight of the TPA particles, is at least about 50 percent less than the 4-CBA content of said solid/liquid mixture, based on the weight of the CTA particles.

15. The process of claim 1 wherein the 4-CBA content of said solid/liquid mixture is greater than about 100 ppmw based on the weight of the CTA particles, wherein the p-TAc content of said solid/liquid mixture is greater than about 250 ppmw based on the weight of the CTA particles.

16. The process of claim 1 wherein the 4-CBA content of said solids-concentrated mixture is less than 50 ppmw based on the weight of the TPA particles, wherein the p-TAc content of said solids-concentrated mixture is less than 150 ppmw based on the weight of the TPA particles.

17. The process of claim 1 wherein said one or more reactants includes para-xylene.

18. A process comprising:
   (a) introducing a feed slurry into a zoned slurry concentrator, said zoned slurry concentrator comprising a single vessel having an agitated zone and a settling zone, wherein the vessel defines a liquids outlet for removing a liquid-concentrated mixture and a solids outlet for removing a solids-concentrated mixture, wherein said feed slurry comprises solid terephthalic acid (TPA) particles and simultaneously subjecting said feed slurry to oxidative digestion and concentration in said zoned slurry concentrator;
   (b) withdrawing a liquid-concentrated mixture from said liquids outlet of said zoned slurry concentrator; and
   (c) withdrawing a solids-concentrated mixture from said solids outlet of said zoned slurry concentrator, wherein the ratio of the solids content of said solids-concentrated mixture to the solids content of said liquid-concentrated mixture is at least about 2:1 by weight.

19. The process of claim 18 wherein said process includes introducing an oxidant stream containing molecular oxygen into said zoned slurry concentrator and/or into said feed slurry upstream of said zoned slurry concentrator.

20. The process of claim 18 wherein said process includes oxidizing one or more reactants in a primary oxidation reactor to thereby produce a solid/liquid mixture, wherein at least a portion of said feed slurry originates from at least a portion of said solid/liquid mixture.

21. The process of claim 20 wherein substantially all of said solid/liquid mixture is employed as said feed slurry.

22. The process of claim 20 wherein said solid/liquid mixture is subjected to at least one intermediate processing step prior to employing at least a portion of said solid/liquid mixture as said feed slurry.

23. The process of claim 22 wherein said at least one intermediate processing step includes one or more of the following steps: (i) solid/liquid separation; (ii) partial liquid replacement; (iii) full liquid replacement; and (iv) oxidative digestion.

24. The process of claim 18 wherein the ratio of the solids content of said feed slurry to the solids content of said liquid-concentrated mixture is at least about 1.5:1 by weight, wherein the ratio of the solids content of said solids-concentrated mixture to the solids content of said feed slurry is at least about 1.5:1 by weight.

25. The process of claim 18 wherein the ratio of the solids content of said solids-concentrated mixture to the solids content of said liquid-concentrated mixture is at least about 10:1 by weight, wherein the solids content of said solids-concentrated mixture is at least about 80 percent by weight and the solids content of said liquid-concentrated mixture is less than about 20 percent by weight.

26. The process of claim 25 wherein the solids content of said feed slurry is in the range of from about 5 to about 40 percent by weight.

27. The process of claim 18 wherein said process includes combining a dilution liquid with said solids-concentrated mixture to thereby produce a diluted mixture, wherein the solids content of said diluted mixture is at least about 25 percent less than the solids content of said solids-concentrated mixture.

28. The process of claim 27 wherein the solids content of said diluted mixture is in the range of from 60 to 90 percent less than the solids content of said solids-concentrated mixture.

29. The process of claim 27 wherein said process includes recovering TPA-containing solids from at least a portion of said diluted mixture.

30. A process comprising:
   (a) oxidizing para-xylene in a primary oxidation reactor to thereby produce an initial solid/liquid mixture containing crude terephthalic acid (CTA) particles;
   (b) subjecting at least a portion of said initial solid/liquid mixture to oxidative digestion in an initial digester to thereby produce an initial digested solid/liquid mixture;
   (c) simultaneously subjecting at least a portion of said initial digested solid/liquid mixture to oxidative digestion and concentration in a zoned slurry concentrator, said zoned slurry concentrator comprising a single vessel having an agitated zone and a settling zone, wherein the vessel defines a liquids outlet for removing a liquid-concentrated mixture and a solids outlet for removing a solids-concentrated mixture;
   (d) withdrawing a liquid-concentrated mixture from said liquids outlet of said zoned slurry concentrator, wherein the ratio of the solids content of said initial digested solid/liquid mixture to the solids content of said liquid-concentrated mixture is at least about 1.5:1 by weight;
   (e) withdrawing a solids-concentrated mixture from said solids outlet of said zoned slurry concentrator; and
   (f) introducing a dilution liquid into said solids-concentrated mixture to thereby produce a diluted mixture having a solids content less than the solids content of said solids-concentrated mixture.

31. The process of claim 30 wherein the solids content of said diluted mixture is at least about 25 percent less than the solids content of said solids-concentrated mixture.

32. The process of claim 30 wherein at least a portion of said dilution liquid is introduced into said solids-concentrated mixture inside said zoned slurry concentrator.

33. The process of claim 30 wherein the ratio of the solids content of said solids-concentrated mixture to the solids content of said initial digested solid/liquid mixture is at least about 5:1 by weight, wherein the ratio of the solids content of said solids-concentrated mixture to the solids content of said liquid-concentrated mixture is at least about 10:1 by weight, wherein the ratio of the solids content of said initial digested solid/liquid mixture to the solids content of said liquid-concentrated mixture is at least about 5:1 by weight.

34. The process of claim 33 wherein the solids content of said solids-concentrated mixture is at least about 80 percent by weight and the solids content of said liquid-concentrated mixture is less than about 20 percent by weight.

35. The process of claim 34 wherein the solids content of said initial digested solid/liquid mixture is in the range of from about 5 to about 40 percent by weight.

\* \* \* \* \*